United States Patent
Rao et al.

(10) Patent No.: US 8,673,292 B2
(45) Date of Patent: Mar. 18, 2014

(54) PURE POPULATIONS OF ASTROCYTE RESTRICTED PRECURSOR CELLS AND METHODS FOR ISOLATION AND USE THEREOF

(75) Inventors: Mahendra S. Rao, Timonium, MD (US); Tahmina Mujtaba, Blaine, MN (US); Yuan Yuan Wu, Salt Lake City, UT (US); Ying Liu, Baltimore, MD (US)

(73) Assignees: University of Utah, Salt Lake City, UT (US); The Government of the United States of America, Washington, DC (US)

( * ) Notice: Subject to any disclaimer, the term of this patent is extended or adjusted under 35 U.S.C. 154(b) by 352 days.

(21) Appl. No.: 12/433,060

(22) Filed: Apr. 30, 2009

(65) Prior Publication Data
US 2009/0220567 A1    Sep. 3, 2009

Related U.S. Application Data

(63) Continuation of application No. 10/502,224, filed as application No. PCT/US03/02356 on Jan. 23, 2003, now abandoned.

(60) Provisional application No. 60/351,036, filed on Jan. 23, 2002.

(51) Int. Cl.
| | | |
|---|---|---|
| *A01N 63/00* | (2006.01) | |
| *C12N 5/071* | (2010.01) | |
| *C12N 5/079* | (2010.01) | |
| *A61K 35/30* | (2006.01) | |

(52) U.S. Cl.
CPC .............. *C12N 5/0622* (2013.01); *A61K 35/30* (2013.01)
USPC ......................................... 424/93.7; 435/368

(58) Field of Classification Search
CPC ............................... C12N 5/0622; A61K 35/30
See application file for complete search history.

(56) References Cited

U.S. PATENT DOCUMENTS

| 5,202,120 | A | 4/1993 | Silver et al. ................. 424/93 U |
| 5,854,207 | A * | 12/1998 | Lee et al. ..................... 424/85.2 |
| 5,874,301 | A | 2/1999 | Keller et al. .................. 435/325 |
| 6,465,249 | B2 | 10/2002 | Reya et al. .................... 435/375 |
| 6,833,269 | B2 * | 12/2004 | Carpenter .................... 435/377 |
| 2002/0164794 | A1 | 11/2002 | Wernet .......................... 435/372 |

FOREIGN PATENT DOCUMENTS

WO    WO/99/28443    *    6/1999

OTHER PUBLICATIONS

Bradbury et al., 1995, Neuroscience, 65: 955-972.*
Ishibashi et al. 2006 "Astrocytes promote myelination in response to electrical impulses" Neuron 49(6):823-832.*
Nobel et al. 1984 "Purified astrocytes promote the in vitro division of a bipotential glial progenitor cell" EMBO 3(10):2243-2247.*
Wang et al. 1993 "Effects of astrocyte implantation into the hemisected adult rat spinal cord" Neuroscience 65(4):973-981.*
Woodbury et al. J. Neurosci. Res. 61:364-370; 2000.*
Raff et al. Nature 303:390-396; 1983.*
Lodie et al. Tissue Eng. 8:739-751; 2002.*
Alfei et al., "Hyaluronate receptor CD44 is expressed by astrocytes in the adult chicken and in astrocyte cell precursors in early development of the chick spinal cord", Eur. J. Histochem. 1999.
Liu et al., "Oligodendrocyte and Astrocyte Development in Rodents:An In Situ and Immunohistological Analysis During Embryonic Development", GLIA 2002 40:25-43.
Marret et al., "Expression and Effects of Hyaluronan and of the Hyaluronan-Binding Protein Hyaluronectin in Newborn Rat Brain Glial Cell Cultures", J. Neurochemistry 1994 62:1285-1295.
Mi et al., "Purification and Characterization of Astrocyte Precursor Cells in the Developing Rat Optic Nerve", The Journal of Neuroscience 1999 19(3):1049-1061.

* cited by examiner

*Primary Examiner* — Jeffrey Stucker
*Assistant Examiner* — Adam M Weidner
(74) *Attorney, Agent, or Firm* — Licata & Tyrrell P.C.

(57) ABSTRACT

An isolated, pure homogeneous population of mammalian astrocyte restricted precursor cells which is CD44 immunoreactive and which generate astrocytes but not oligodendrocytes is provided. Methods for isolating and using these mammalian astrocyte restricted precursor cells are also provided.

9 Claims, No Drawings

PURE POPULATIONS OF ASTROCYTE RESTRICTED PRECURSOR CELLS AND METHODS FOR ISOLATION AND USE THEREOF

INTRODUCTION

This patent application is a continuation of U.S. application Ser. No. 10/502,224, filed May 17, 2005, which is the U.S. National Stage of PCT/US03/02356, filed Jan. 23, 2003, which claims the benefit of priority from U.S. Provisional Application Ser. No. 60/351,036, filed Jan. 23, 2002, which are herein incorporated by reference in their entirety.

This invention was supported in part by funds provided by the National Institutes of Health (Grant No. 5R29NS35087-05). The U.S. Government has certain rights in this invention.

FIELD OF THE INVENTION

The present invention relates to a homogeneous, pure population of mammalian astrocyte restricted precursor cells which are CD44 immunoreactive and generate astrocytes but not oligodendrocytes. The present invention is also related to methods for isolating a homogeneous, pure population of these mammalian astrocyte restricted precursor cells. In addition, the present invention relates to use of mammalian astrocyte restricted precursor cells in the development of new transplantation techniques and to enhance myelination and/or reduce necrosis and glial scar formation upon administration to animals. The astrocyte restricted precursor cells and pharmaceutical compositions comprising the same, may thus be used to treat disorders of the nervous system resulting from trauma or disease which have in some way damaged the nerve tissue. These cells are also useful in identifying mammalian genes specific to selected stages of development.

BACKGROUND OF THE INVENTION

Neural development has been well characterized in rodents. Multipotent cells which are nestin immunoreactive and capable of differentiating into astrocytes, neurons, and oligodendrocytes have been identified by multiple investigators at various stages of development. In addition to multipotent precursors, other more restricted precursors have also been identified. Different populations of cells can be distinguished by differences in culture conditions, self-renewal capability, as well as in their ability to integrate and to differentiate following transplantation.

Similar studies using human tissue are indicative of the existence of multiple types of neural precursors as well. Multipotent human neural stem cells (hNSCs) have been isolated from fetal and adult tissue (Chalmers-Redman et al. Neuroscience 1997 76:1121-1128; Svendsen et al. J. Neuroscience Methods 1998 85:141-152; Vescovi et al. Exp. Neurology 1999 156:71-83; Carpenter et al. Exp. Neurology 1999 158:265-278; Quinn et al. J. Neuroscience Res. 1999 57:590-602; Piper et al. J. Neurophysiology 2000 84:534-548). These cells give rise to glia and neurons, can be grown under different culture conditions, and show different growth factor requirements.

Human neuron restricted precursors have also been described (Piper et al. J. Neurophysiol. 2000 84:534-548). Piper et al. used E-NCAM immunoreactivity to isolate neuronal precursor cells while Goldman and colleagues used neuron specific promoters to isolate neuronal precursors (Roy et al. Nat. Med. 2000 6(3):271-7; Roy et al. J. Neurosci. Res. 2000 59(3):321-31; Wang et al. Dev. Neurosci. 2000 22(1-2): 167-76). Human neuronal restricted precursor cells have been isolated from the adult ventricular zone and hippocampus as well as from fetal tissue at multiple stages of development. These cells differ from human neuroepithelial cells by their expression of early neuronal markers such as NCAM, alpha-1 tubulin and beta-III tubulin.

Proliferative adult human oligodendrocyte precursors have been isolated from adult human white matter (Prabhakar et al. Brain Res. 1995 672(1-2):159-69, Raine et al. Lab. Invest. 1981 45(6):534-46; Scolding et al. Neuroreport 1995 6(3):441-5; Scolding et al. Neuroscience 1999 89(1):1-4) using cell surface markers. Others have used promoter-reporter constructs to isolate oligodendrocytes and their precursors from fetal and adult tissue. A2B5 immunoreactivity has been utilized to isolate glial precursors that are capable of differentiating into astrocytes and oligodendrocytes (U.S. Pat. No. 6,235,527).

Quinn and colleagues (J. Neurosci. Res. 1999 57:590-602) describe a mixed population of multipotent stem cells that can become altered in their properties after prolonged culture. These cells have been suggested to be astrocyte restricted precursor cells. However, oligodendrocyte differentiation has not been tested. Further, no information on antigenic expression, cytokine dependence, response to growth factors, expression of GFAP/S100, or A2B5 is available. The cells of Quinn et al. were obtained by sequentially passaging multipotent stem cells from cultured human spinal cord tissue.

A putative astrocyte precursor cell has also been described by Barres et al. (J. Neurosci. 1999 19(3):1049-61). This cell was isolated from the optic nerve and its existence in any other part of the brain is unknown. This cell is A2B5 immunoreactive and thus resembles the oligodendrocyte precursor O2A. The cells can be distinguished from the O2A cells mainly by their failure to develop into oligodendrocytes under conditions in which the O2A cells readily generate oligodendrocytes. This cell is Pax-6-positive and dies when exposed to serum. Immunoreactivity with CD44 is unknown.

Siedman et al. (Brain Res. 1997 753(1):18-26) have also described an astrocyte cell line derived by immortalization of a glial precursor cell. Little information on this immortalized precursor cell is available and its antigenic characteristics and ability to differentiate into neurons have not been disclosed.

SUMMARY OF THE INVENTION

The present invention is directed to astrocyte restricted precursor cells, pharmaceutical compositions comprising the same, and methods of utilizing the astrocyte restricted precursor cells to treat mammals with damage to the nervous systems. The astrocyte restricted precursor cells of the present invention are not immortalized. These cells do not express A2B5. Further, these cells differ from stem and progenitor cell populations in their expression of CD44 and their ability to differentiate into astrocytes under conditions in which other populations differentiate into neurons or oligodendrocytes.

Thus, one aspect of the present invention relates to an isolated, pure homogeneous population of mammalian astrocyte restricted precursor cells which is CD44 immunoreactive and can generate astrocytes but not oligodendrocytes.

Another aspect of the present invention relates to a method for isolating a pure homogeneous population of mammalian astrocyte restricted precursor cells. In the method of the present invention, the pure homogeneous population of astrocyte restricted precursor cells is isolated from a heterogeneous or mixed population of mammalian cells via CD44 immunoreactivity.

Another aspect of the present invention relates to methods for development of new transplantation techniques using these mammalian astrocyte restricted precursor cells.

Another aspect of the present invention relates to pharmaceutical compositions comprising the mammalian astrocyte restricted precursor cells and methods of using these compositions to treat patients with damage of the nervous system. In one embodiment, the compositions and methods are used to enhance myelination of mammalian neuronal cells. In another embodiment, the compositions and methods are used to reduce glial scar formation and necrosis.

Another aspect of the present invention relates to methods for identifying mammalian genes specific to selected stages of development using these astrocyte restricted precursor cells.

DETAILED DESCRIPTION OF THE INVENTION

For cell replacement in the nervous system, differentiated cells are ultimately required. However, extensive studies have shown that differentiated cells do not survive well following transplantation. Therefore, some researchers have focused their efforts on use of precursor cells which have been shown to survive and integrate into the intact or damaged brain.

The present invention relates to a pure, homogeneous population of mammalian astrocyte restricted precursor cells which can be isolated from various sources of mammalian neural tissue and/or cells including, but not limited to, mammalian embryonic or fetal tissue, mammalian embryonic stem (ES) cell cultures, and glial restricted precursor cells. The present invention also relates to methods for isolating a pure, homogeneous population of astrocyte restricted precursor cells from such tissues and cells.

For purposes of the present invention, by "pure" it is meant a population of cells in which greater than 95%, more preferably 99%, exhibit the same characteristics.

In a preferred embodiment, the mammalian tissue or cells from which the astrocyte restricted precursor cells are isolated is either rodent or human. However, as will be understood by those of skill in the art upon reading this disclosure, the methods for isolation taught herein are also routinely adaptable to cells or tissues from other mammals including, but not limited to, non-human primates, equines, canines, felines, bovines, porcines, ovines, lagomorphs, and the like As demonstrated herein, the astrocyte restricted precursor cells of the present invention express CD44. Prior to differentiations these cells also express nestin. Unlike the putative astrocyte restricted cells of Barres et al. (J. Neurosci 1999 19(3):1049-61), the astrocyte restricted precursor cells of the present invention do not express A2B5. Nor do the cells of the present invention express PSANCAM. The cells of the present invention grow well in FGF and EGF. The CD44-positive cells of the present invention do not express GFAP, vimentin or S-100 initially, but have the capacity to differentiate into GFAP, vimentin and/or S-100 positive cells. Upon differentiation, the cells of the present invention maintain their CD44 immunoreactivity but lose expression of nestin. Thus, the CD44 positive cells of the present invention can be readily distinguished from glial-restricted precursor cells, multipotent stem cells, neuronal precursors and the putative astrocyte precursor described by Barres et al. (J. Neurosci. 1999 19(3):1049-61) based on antigen expression, cytokine dependence and differentiation ability. See Table 1 which provides a comparison of characteristics of the cells of Barres et al with the astrocyte restricted precursor (ARP) cells of the present invention.

TABLE 1

| Characteristic | Barres et al. | ARP Cells of Present Invention |
| --- | --- | --- |
| A2B5 Expression | ++ | -- |
| CD44 Expression | n.d. | ++ |
| Pax-6 Expression | ++ | -- |
| Clonal analysis | n.d. | ++ |
| Transplant experiments | n.d. | ++ |
| Serum Exposure | death | differentiation | n.d. = not determined

The astrocyte restricted precursor cells are present in the developing mammalian brain prior to acquisition of GFAP immunoreactivity. In addition, the CD44+ astrocyte restricted precursor cells can be generated from glial-restricted precursors (GRP) and can be distinguished from GRP cells by antigen expression, cytokine dependency and differentiation ability.

Clonal analysis indicates that a subset of nestin+ cells that are GFAP− when grown in culture differentiate solely into astrocytes. This subset is quite large and constitutes approximately 11% of the cells analyzed.

A variety of markers were examined to identify a cell surface marker that would label this nestin+/GFAP− population of cells. It was found that CD44 is specific for this glial population. CD44 expression co-localized with astrocytic markers such as GFAP and S-100. CD44+ cells were RC1 negative and did not co-express A2B5. A small subset of the CD44+ cells were nestin immunoreactive but GFAP negative, thus indicating that these cells represented an astrocyte precursor cell population.

While the number of CD44 positive cells is small, generally in the range of 1-10% of the total number of cells present at any stage of development from E15 to adult, it increases after culture in conditions that promote astrocyte differentiation. CD44 positive cells divide in culture and express low levels of GFAP. Expression of GFAP increases after differentiation while the expression of CD44 is down regulated. CD44 positive cells do not express A2B5 or PLP and, thus, can be distinguished from the bipotential glial-restricted precursor cell. While CD44 expression has been described in other cell types such as macrophages and astrocytes following injury, under the differentiation conditions used herein, CD44 expression was limited to astrocytes and, thus, can be used in accordance with procedures taught herein to identify astrocyte restricted precursor cells.

Thus, as demonstrated herein, CD44 expression can be used to identify and isolate astrocyte restricted precursor cells from various sources of neural tissue including, but not limited to, mammalian ES cell cultures and mammalian fetal or embryonic tissue as well as glial-restricted precursor cells or GRPS methods for isolating glial restricted precursor cells are described in U.S. Pat. No. 6,235,527 the teachings of which are herein incorporated by reference in their entirety. This population of astrocyte restricted precursor cells is not immortalized. Further, population of cells does not express A2B5 and differs from stem and progenitor populations in its expression of CD44 and its ability to differentiate into astrocytes under conditions in which other populations differentiate into neurons or oligodendrocytes.

Various methods for isolating the CD44 positive astrocyte restricted precursor cells from mixed populations of cells can be used.

In one embodiment, mammalian neural tubes are dissociated at a stage after astrocyte development, for example week 10 onward in humans or after E16 in rodents, and dissociated cells are triturated to a single cell suspension and labeled with an anti-CD44 antibody. Labeled cells are visualized using a fluorescently labeled secondary antibody targeted to the first antibody and labeled cells are isolated using a selection process.

Examples of selection processes useful in the present invention include, but are not limited to immunopanning, magnetic bead sorting and/or FACS sorting. Detailed magnetic bead and FACS sorting protocols are well known in the art and can be routinely adapted to use of CD44 as the selection marker. Further, as will be understood by those of skill in the art upon reading this disclosure, negative as well as positive selection methods can be used. Thus enrichment of the astrocyte restricted precursor cells of the present invention can be achieved by reselecting from a mixed population cells that express CD44 but do not express A2B5 or E-NCAM and vice versa. Positive and negative selection processes can be used in any sequence and antibodies with a binding profile similar to A2B5 or E-NCAM can be used.

In another embodiment, neural tubes are dissociated at any stage after neural tube closure, for example E8.5 in mouse, E10.5 in rat, and week 5 gestation in human, and cells are maintained in adherent culture for 5 to 40 days. Cells are then removed from culture and CD44 positive cells are isolated via a selection process as described in the preceding paragraph.

In another embodiment, A2B5+ cells are isolated. Cells are then induced to differentiate in culture by growth in astrocyte promoting conditions. By astrocyte promoting conditions it is meant to include, but is not limited to, addition of bone morphogenetic proteins (BMPs), oncostatin M, serum, Leukemia Inhibitory Factor/Ciliary Neurotrophic Factor (LIF/CTNF) and other members of the cytokine family such as interleukin-6 either singly or in combination for a minimum period of three days. In a preferred embodiment these agents are added at concentrations in the range of 1-5 ng/mL. CD44+ cells are then isolated via a selection process as described above.

Recently, human fetal tissue derived neural cells have become available through commercial sources such as Cambrex (East Rutherford, N.J.), Clonexpress (Gaithersberg, Md.), ScienCell Research Laboratories (San Diego, Calif.) and Clonetics (San Diego, Calif.). These cells serve as a source of neural tissue and/or cells for isolation of the mammalian astrocyte restricted precursor cells of the present invention in accordance with the methods taught herein.

Use of human ES cell lines as a source of the astrocyte restricted precursor cells was also demonstrated in three human cell lines (H1, H7, H9). Human ES cells have been previously shown to differentiate into neuronal progenitors that subsequently generate differentiated neurons (Carpenter et al. Exp. Neurol. 2001 172(2):383-97). In the present invention, dividing precursor cells that expressed neuronal or glial markers were first identified in ES cells. Differentiation conditions were similar to those described herein and used for generating neurons. Specifically, the first stage of differentiation of the ES cells was induced by the formation of embryonic bodies (EBs) in FBS media with or without 10 µM all trans-RA. After 4 days in suspension, EBs were plated onto fibronectin coated plates in defined proliferation media supplemented with 10 ng/mL hEGF, 10 ng/mL hbFGF, 1 ng/mL hPDGF-AA, and 1 ng/mL hIGF-1. In these conditions, the EBs adhered to the plates and cells began to migrate and proliferate on the plastic, forming a monolayer. After 3 days in these conditions many cells with neuronal morphology were present. Similar results were found with each human ES cell line.

Multiple types of dividing cell populations can be identified in cultures of differentiating ES cells based on antibodies that recognize cell surface epitopes. These include A2B5+ cells, PSANCAM+ cells and CD44+ cells. Double labeling experiments following differentiation showed that the CD44+ cells of the ES cells were a unique population of cells that were similar morphologically, antigenically and in their ability to differentiate into astrocytes to the astrocyte restricted cells of the present invention isolated from other sources of neural tissue and cells.

The astrocyte restricted precursor cells of the present invention have a variety of uses.

For example, these cells can be used in nonhuman mammalian models to develop new transplantation techniques.

In addition, these cells can be used therapeutically in mammals, more preferably humans, in diseases characterized by neural damage and more particularly astrocyte degeneration. In particular, administration of the astrocyte restricted precursor cells of the present invention is expected to be useful in enhancing myelination of neurons. These cells are also useful in identifying new drugs which enhance survival and proliferation of these cells upon administration.

The cells can also be used in the reduction of scars. It is well known that fetal astrocytes can incorporate into the brain when transplanted. Fetal cells, as opposed to adult cells, reduce adult glial cell proliferation and scar formation, thereby promoting repair. Astrocyte restricted precursor cells of the present invention can be administered at or near a lesioned site or area of damage one week to several weeks after injury to reduce endogenous adult glial cell proliferation and reduce scar formation.

Accordingly, the present invention also relates to pharmaceutical compositions comprising these astrocyte restricted precursor cells for use in treatment of mammals with neural damage. In a preferred embodiment, the cells are provided in injectable form or on implants to promote directed axon regeneration and reduce glial scar formation in the forebrain, and/or in damaged spinal axons of the central nervous system. Such compositions are useful in promoting CNS nerve regeneration and/or enhancing myelination and/or reducing glial scar formation. Compositions comprising astrocyte restricted precursor cells can be applied, in various different formulations as described infra, to regions or areas of nerve damage. Such compositions can be administered to mammals having nervous system damage resulting from various causes including, but not limited to, trauma, surgery, ischemia, infection, metabolic disease, nutritional deficiency, malignancies and paraneoplastic syndromes, toxic agents, and degenerative disorders of the nervous system. Examples of neurodegenerative disorders which can be treated using compositions of the present invention include, but are not limited to, Alzheimer's disease, Parkinson's disease, Huntington's chorea, amyotrophic lateral sclerosis, progressive supranuclear palsy and peripheral neuropathies. Compositions comprising the astrocyte restricted precursor cells of the present invention can also be applied to a wound to reduce scar formation. For example, following surgery, a composition comprising these cells can be applied in accordance with the presence invention to reduce scar formation from a lesion due to, for example, arteriovenous malformation, necrosis, bleeding, and craniotomy, which can secondarily lead to epilepsy. The compositions of the present invention can also be used in the treatment of epilepsy by stabilizing the epileptic focus and reducing scar formation.

Pharmaceutical compositions of the present invention comprise an effective amount of the isolated astrocyte restricted precursor cells of the present invention and a pharmaceutically acceptable carrier. By "effective amount" it is meant a composition comprising approximately 100,000 to about one million cells. As will be understood by one of skill upon reading this disclosure however, cell number may vary depending upon the selected site of administration. Examples of pharmaceutically acceptable carriers include, but are not limited to liquid vehicles such as sterile saline, buffered saline, dextrose and water and semi-liquid or gel-like vehicles which may further comprise a media which impedes, at least in part, the mobility of the cells so as to localize the cells at the site of damage. Alternatively, pharmaceutically acceptable carriers may comprise a solid vehicle such as an implant seeded or coated with the cells.

The pharmaceutical compositions can be delivered by a wide range of methods to promote CNS nerve regeneration, enhance myelination and/or reduce scar formation. Exemplary methods adaptable for use with the compositions of the present invention are set forth in U.S. Pat. No. 5,202,120, the teachings of which are herein incorporated by reference in their entirety.

In one embodiment, the cells are delivered by direct application, for example, by direct injection of the cells in a vehicle into or near the site of nerve damage. In this embodiment, it may be preferred to deliver the cells in a vehicle comprising a media which impedes, at least in part, the mobility of the cells so as to localize the cells at the site of damage. Examples of media which can impede cell mobility include, but are not limited, pastes or gels, such as biodegradable gel-like polymers of fibrin or hydrogels. These semi-solid media also provide the advantage of impeding migration of scar producing mesenchymal components such as fibroblasts into the site.

In another embodiment, the cells can be delivered via a pharmaceutical compositions comprising a polymer implant or using surgical bypass techniques. For example, the astrocyte restricted precursor cells can be seeded or coated onto a polymer implant. Various polymer implants with differing composition, geometries and pore size which can be used in this embodiment have been described. Examples include, but are in no way limited to, implants comprising nitrocellulose, polyanhydrides and acrylic polymers. In a preferred embodiment, an implant with a pore size of at least 0.45 μm is used.

The geometry of the implant is selected based upon its intended use at the damage site. For example, an elongated triangular implant may be selected to promote nerve regeneration into the spinal cord dorsal root entry zone while a pentagonal-shaped implant may be used to promote nerve regeneration in the corpus callosum.

In another embodiment, the polymers may serve as synthetic bridges over which nerve regeneration is promoted and scar formation reduced by application of the astrocyte restricted precursor cells at the ends or in the vicinity of the ends of the synthetic bridge. For example, an acrylic polymer tube with astrocyte restricted precursor cells of the present invention at one or more ends, or throughout the tube, can be used to bridge lesions rostrally or bypass lesions, for example, of the spinal cord, over which nerve regeneration can be induced. Examples of such tubes are set forth in European Patent Publication 286284, and in references by Aebischer et al. (Brain Res. 1988 454:179-187 and Prog. Brain Res. 1988 78:599-603) and Winn et al. (Exp. Neurol. 1989 105:244-250).

The cells of the present invention can also be used in combination with surgical bypass techniques to promote nerve regeneration and/or to reduce scar formation in a selected region. Examples of such techniques which can be routinely adapted to use with the compositions of the present invention are set forth in U.S. Pat. No. 5,202,120, which is herein incorporated by reference in its entirety.

The astrocyte restricted precursor cells of the present invention are also useful in the identification of genes specific to selected stages of development. In one embodiment, the cells can serve as a source of mRNA for generation of cDNA libraries that are specific to the stage development of the cells.

The cells can also be used in the generation of cell lines and cell-specific antibodies for use therapeutically and diagnostically as well.

The following nonlimiting examples are provided to further illustrate the present invention.

EXAMPLES

Example 1

Culture of Human Neural Stem Cells

Human neural progenitor cells derived from fetal tissue were acquired from Cambrex. Frozen aliquots of cells were thawed and plated on fibronectin/laminin-coated multiwell dishes in Neural Progenitor Cell Basal Medium (NPBM, Cambrex) supplemented with human recombinant basic fibroblast growth factor, human recombinant epidermal growth factor, "neural survival factors", 5 mg/mL gentamicin, and 5 mg/mL amphotericin-B (Singlequots, Cambrex). Cultures were incubated at 37° C., 5% $CO_2$ and fixed 24 hours later. These wells were subsequently processed for immunocytochemistry to assess the starting population of Cambrex cells. In parallel, Cambrex cells were thawed and immediately plated on fibronectin/laminin-coated flasks (Greiner) and cultured in Neuroepithelial Precursor (NEP) medium that consisted of DMEM-F12 (Life Technologies) supplemented with additives as described by Bottenstein and Sato, basic fibroblast growth factor (bFGF, 10 ng/ml, Peprotech, Rocky Hill, N.J.), and chick embryo extract (CEE, 10%). Unattached cells typically formed floating spheres. After 24 hours in culture, spheres were removed, gently triturated, and re-combined with the attached cells. NEP media was exchanged every other day.

Example 2

Isolation of Human Neuroepithelial Precursor Cells (hNEPs)

After 5 days in culture, immunopanning and flow-activated cell sorting were used to remove ENCAM+, NG2+, and A2B5+ cells. Briefly, cells were treated with 5 mM EDTA (Life Technologies) and the suspension plated on an ENCAM antibody (5A5, Developmental Studies Hybridoma Bank)-coated dish to allow binding of all ENCAM+ cells to the plate. ENCAM antibody-coated dishes were prepared by sequentially coating tissue culture dishes with an unlabeled anti-mouse IgM antibody (10 mg/ml) overnight, rinsing dishes with DPBS, followed by coating with 5A5 hybridoma supernatant for 1-3 hours at 37° C. Plates were washed twice with DPBS prior to plating neural progenitor cells. After a 30 minute exposure period, unbound cells (eNCAM− cells) were removed and plated onto a dish coated with antibodies to NG2 for 30 minutes. NG2 panning dishes were made by coating dishes with an NG2 antibody (1:100) for 1-3 hours at 37° C. The supernatant was then removed (ENCAM−/NG2− cells) and immunostained for A2B5. Cells were exposed to antibodies to A2B5 (1:2, Developmental Studies Hybridoma Bank) in NEP media for 1 hour at 37° C., 5% $CO_2$. A secondary goat anti-mouse IgM-PE labeled antibody was then applied for 1 hour to stain the membranes of live A2B5+ cells. All cells were then sent through a flow-activated cell sorter to remove the population of A2B5+ cells. After sorting, the negative population (human NEPs) was propagated in NEP media on fibronectin/laminin coated T-75 flasks prior to transplantation studies. NEP media was exchanged every other day.

Example 3

Generation of Neurons, Oligodendrocytes, and Astrocytes from hNEPs

Panned/sorted populations of human NEPs were plated on fibronectin/laminin-coated 12 mm coverslips in various conditions to promote differentiation. To induce neuronal differentiation, cells were exposed to bFGF (10 ng/ml) and NT3 (10 ng/ml, Peprotech). After 5 days in culture, fixed cultures were stained using antibodies to beta-III tubulin to assess the capacity of these cells to differentiate into neurons. For oligodendrocyte differentiation, cells were plated in a bFGF (10 ng/ml)-containing medium for 2 days and then were switched to a medium containing PDGF (10 ng/ml, Upstate Biotech., Waltham, Mass.) and T3 (50 nM) for 7 days. Antibodies to O4, GalC and MBP were used to identify oligodendrocytes in culture. For astrocytic differentiation, cells were cultured for 5 days in the presence of fetal calf serum (10%, Life Technologies). Astrocytes were identified using antibodies to CD44, GFAP and S-100.

Example 4

Clonal Cultures and Clonal Propagation

Mixed cell cultures of human fetal cells (12-22 weeks of gestation) were obtained from Clonetics and plated in T80 flasks in the presence of bFGF and CEE (10%). After 3 days in culture cells were labeled with A2B5 and NG-2. Immunonegative cells were collected by FACS sorting analysis and replated into flasks in the presence of bFGF and CEE. After 24 hours cells were labeled with E-NCAM, sorted by FACS and negative cells were replated at a clonal density in 10 cm dishes in the presence of bFGF and CEE. Control dishes were labeled after 24 hours with A2B5, E-NCAM, GFAP and NG-2. At that time point, 97% of all cells do not express any of the differentiation markers tested. Single cells were grown at a clonal density of 50-200 cells/35 mm dish). Cells were maintained in FGF and CEE for 8-10 days and then CEE was withdrawn to initiate differentiation. For oligodendrocyte differentiation cultures were exposed to PDGF and thyroid hormone. After 5-7 days cultures were labeled with antibodies against GFAP and beta-III tubulin to determine differentiation into astrocytes and neurons, respectively. Generation of oligodendrocytes was assessed 7 to 15 days after the initiation of differentiation. Neuronal and glial differentiation was assessed using antibodies against GFAP, and beta-III tubulin. For oligodendrocyte differentiation, cultures were exposed to PDGF and thyroid hormone and differentiation was assessed using antibodies to O4 and Gal-C.

Example 5

Generation of Neurons, Oligodendrocytes, and Astrocytes from hNEPs

Panned/sorted populations of human NEPs were plated on fibronectin/laminin-coated 12 mm coverslips in various conditions to promote differentiation. To induce neuronal differentiation, cells were exposed to bFGF (10 ng/ml) and NT3 (10 ng/ml, Peprotech). After 5 days in culture, fixed cultures were stained using antibodies to beta-III tubulin to assess the capacity of these cells to differentiate into neurons. For oligodendrocyte differentiation, cells were plated in a bFGF (10 ng/ml)-containing medium for 2 days and then were switched to a medium containing PDGF (10 ng/ml, Upstate Biotech., Waltham, Mass.) and T3 (50 nM) for 7 days. Antibodies to O4, GalC and MBP were used to identify oligodendrocytes in culture. For astrocytic differentiation, cells were cultured for 5 days in the presence of fetal calf serum (10%, Life Technologies). Astrocytes were identified using antibodies to CD44, GFAP and S-100 (Morita et al. Dev. Neurosci. 1997 19:210-218; Gomes et al. Braz. J. Med. Biol. Res. 1999 32:619-631).

Example 6

Human ES Cell Culture

Male (H1) and female (H7 & H9) huES cell lines were maintained on MATRIGEL in MEF (primary mouse embryonic fibroblasts) conditioned medium (CM). CM was generated from huES cell media (ESM) comprised of 80% Knockout DMEM (Gibco), 20% Knockout Serum replacement (Gibco), 0.1 mM beta-mercaptoethanol, 1 mM glutamine, 1% non-essential amino acids, supplemented with 4 ng/mL hbFGF (Gibco). Cultures were passaged by incubation in 200 units/ml collagenase IV (Gibco) for about 5-10 minutes at 37° C. and then gently dissociated into small clusters in CM. Cells were passaged about once every week. Conditioned media was generated from MEF and collected daily and used immediately for feeding HuES cultures. Before addition to the HuES cultures this conditioned media was supplemented with an additional 4 ng/ml of hbFGF (Gibco). Cells for generating CM were refed with ESM daily and used for 7-10 days.

Example 7

Differentiation of huES Cells

Embryoid bodies (EBs) were formed from undifferentiated ES cultures harvested by incubation with 200 u/mL collagenase at 37° C. for 5-10 minutes. The cells were gently scraped from the dish and resuspended in ultra low attachment polystyrene plates (Corning) in media composed of KO-DMEM, 20% FBS, 1% non-essential amino acids, 1 mM glutamate and 0.1 mM beta-mercaptoethanol. In some experiments, 10 µM all-trans retinoic acid was added to the EBs in suspension. After 4 days in suspension, EBs were plated onto poly-l-lysine/FN coated plates in proliferation media comprised of DMEM/F12 with B27 and N2 supplements (Gibco) and 10 ng/mL hEGF, 10 ng/mL hbFGF (Gibco), 1 ng/mL hPDGF-AA (R&D Systems), 1 ng/mL hIGF-1 (R&D Systems). After 3 days in these conditions, the cells were harvested with trypsin and replated in differentiation media comprised of Neurobasal media supplemented with B27, 10 ng/mL hNT-3 (R&D Systems) and 10 ng/mL hBDNF (R&D Systems). These cultures were fed 3 times per week and fixed after 14-21 days.

Example 8

Immunocytochemistry

Cultures were stained using antibodies against A2B5 (1:2, Developmental Studies Hybridoma Bank), AC133/2 (1:100, Miltenyi Biotec, Auburn, Calif.), beta-III tubulin (1:1000, Sigma), E-NCAM (1:2, 5A5, Developmental Studies Hybridoma Bank), GFAP (1:2000, Dako, Carpinteria, Calif.), NG2 (1:100) and O4 (1:2, Developmental Studies Hybridoma Bank). Following fixation, cultures were treated with 0.5% Triton X-100 (Sigma) in PBS for 2 minutes to access intracellular antigens. Fixed coverslips or plates were then treated with primary antibodies in a blocking solution containing Hank's balanced salt solution and 5% calf serum for 1 hour at room temperature. Following 3 washes with PBS, cultures were incubated in the appropriate secondary antibodies (1:220) conjugated to either Texas Red or Alexa 488 (Molecular Probes, Eugene, Oreg.) for 1 hour at room temperature. AC133/2 staining required amplification with a biotinylated secondary antibody, followed by a streptavidin-alexa 488 conjugated tertiary antibody. All cultures were counterstained with DAPI (Molecular Probes) to identify cell nuclei.

What is claimed is:

1. An isolated population of mammalian precursor cells which generate astrocytes but not oligodendrocytes, said cells being nestin$^+$, A2B5$^-$, and E-NCAM$^-$ or Pax-6$^-$.

2. A pharmaceutical composition comprising the isolated population of mammalian precursor cells of claim 1 and a pharmaceutically acceptable carrier.

3. The pharmaceutical composition of claim 2 wherein the pharmaceutically acceptable carrier is an implant seeded or coated with the mammalian precursor cells.

4. A method for treating damaged neural cells comprising administering to the damaged neural cells the pharmaceutical composition of claim 2.

5. The method of claim 4 wherein the pharmaceutical composition is administered to the damaged neural cells by direct injection to the damaged neural cells.

6. The method of claim 4 wherein the pharmaceutical composition comprises an implant seeded or coated with the mammalian precursor cells.

7. The method of claim 6 wherein the pharmaceutical composition is implanted at or near a site of damaged neural cells.

8. The method of claim 4 wherein administering the pharmaceutical composition to the damaged neural cells enhances myelination of the damaged neural cells.

9. The method of claim 4 wherein administering the pharmaceutical composition to the damaged neural cells reduces scar formation.

* * * * *